United States Patent [19]

Barberet et al.

[11] Patent Number: Plant 6,710

[45] Date of Patent: Apr. 4, 1989

[54] CARNATION NAMED LONTOYO

[75] Inventors: Nicole Barberet; Yves Ducloux, both of Antibes, France

[73] Assignee: Laboratoire de Physiologie Vegetale de la Londe, La Londe, France

[21] Appl. No.: 100,719

[22] Filed: Sep. 24, 1987

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation variety having small, bright orange blooms produced profusely at intermittent intervals from spring through fall in clusters appearing at the upper portion of strong, upright and rigid stems, the flowers being distinguished by their relatively small size and the orange coloration of the petals, which are striated with longitudinally extending, red lines, and the plant itself being distinguished by its tall, vigorous and upright growth habit with moderately abundant foliage.

1 Drawing Sheet

BACKGROUND OF THE NEW PLANT

This new carnation variety originated as a seedling resulting from our crossing of plants selected from our collection of carnation plants maintained by us for breeding purposes at La Londe, Les Maures, France, our object in making this crossing being to develop a new spray carnation having blooms of good quality and color and having resistance to *Fusarium oxysporum.* Our new plant was reproduced by cuttings with such satisfactory results that further propagation was directed to be carried on through successive generations, also by means of cuttings, from previous plants of the new variety produced in the same manner. From observation of our propagation of the new seedling, we are satisfied that the novel characteristics of its blooming and growth habits would remain true from generation to generation and appear to be firmly fixed.

DESCRIPTION OF THE DRAWING

Our new variety of spray carnation is illustrated by the accompanying full color photographic drawing, which shows the upper portions of typical spray stems bearing buds and flowers at various stages of maturity, the colors shown being as nearly true to those specified herein as is reasonably possible to obtain by professional photographic procedures.

DESCRIPTION OF THE NEW PLANT

The following is a detailed description of our new spray carnation plant based upon observations of greenhouse plants grown at La Londe, Les Maures, France, the color designations being according to The R.H.S. Colour Chart published by The Royal Horticultural Society of London, England.

THE PLANT

Origin: Seedling.

Parentage:

*Seed parent.*—Stock Variety 75 MR 16.

*Pollen parent.*—Stock Variety 80 MC 43. These parent varieties were selected by us from our collection of breeding plants and each is individually identified in our permanent records maintained in our offices at La Londe.

Classification:

*Botanic.*—*Dianthus caryophyllus.*

*Commercial.*—Spray Carnation.

Form: A bush of tall spray shape comprising at least four stems emitted from the main stem near the ground after pinching it at about 15 cm. from the ground.

Branching character: Moderately branched.

Growth: Vigorous, upright and rigid.

Foliage:

*Quantity.*—Moderately abundant.

*Number of leaves.*—At least 120.

*Size of leaf.*—About 11 cm. long and about 0.7 cm. wide, at the 7th node.

*Leaf shape.*—Lanceolate with entire margins.

*Texture.*—Leathery.

*Color.*—189-B on both upper and lower sides.

*Leaflets.*—None.

*Ribs and veins.*—Hardly noticeable.

*Rachis.*—Hardly noticeable.

THE BUD

Size: Small.

*Diameter.*—Averages about 1 cm.

*Length.*—Averages about 2.6 cm.

Shape: Cylindrical and long.

Opening rate: Normal for carnations.

Color of petals: When sepals first divide and when petals begin to unfurl, the color is the same as at full bloom.

Sepals:

*Number.*—Five.

*Shape.*—Somewhat oval with a mucronate apex and joined together at the base. The sepals are hooded over the bud before dividing and stand up as the flower opens.

*Color.*—Inside — 145-C. Outside — 144-C and 138-B.

*Striae.*—Longitudinal.

Calyx: Of medium size and of long, cylindrical shape.

*Splitting.*—The calyx does not split.

*Aspect.*—Smooth.

Flower Stem:

*Length.*—About 57 cm. (in average).

*Color.*—189-A/B.

*Character.*—Erect and rigid.

THE FLOWER

Blooming habit: Recurrent, blooming profusely from spring through fall with a tendency to give fewer blooms in the fall.

Size of flower: Small.

*Diameter.*—Averages about 5 cm.

*Depth.*—Averages about 4.4 cm.

Borne: In a cluster.

Shape: When bloom first opens, high centered. When bloom matures, dome shaped.

Petalage:

*Number of petals.*—About 29 (in average).

*Arrangement.*—Imbricated.

*Form.*—Fan shaped with lightly ruffled edges and with fine serrations at the apex.

*Texture.*—Leathery.

*Aspect.*—Satiny.

*Color.*—Outer petals and inside petals: Body — Between 30-D and 29-A striated with 44-B. Base — Greenish. Reverse side — Between 24-C and 26-C.

Petaloids:

*Number.*—Less than four.

*Size.*—Smaller than the petals.

*Color.*—The same as the petals.

Flower stem:

*Length.*—About 57 cm.

*Color.*—189-A and 189-B.

*Character.*—Upright and of good strength.

Discoloration after full bloom: Weak.

Persistence: The flowers hang on and dry.

Fragrance: Strong.

Disease resistance: Resistant to *Fusarium oxysporum* as observed INRA-Antibes 06-France.

Lasting quality:

*As a cut flower.*—At least ten days in vase keeping.

REPRODUCTIVE ORGANS

Stamens:

*Number.*—Twelve.

*Arrangement.*—Around the ovary.

*Anthers.*—Size: Less than 0.4 cm. Color: Whitish.

*Filiments.*—Color: Whitish.

Pistils:

*Number.*—3 to 4.

*Color.*—Whitish.

*Stigmas.*—Color: Lightly pinkish.

Ovaries: Hardly ribbed.

This new spray carnation variety most nearly resembles the variety 'Lonforem' (U.S. Plant Pat. No. 5,444) but differs by having a brighter color, less deeply serrated form of petals, and being smaller in flower size.

We claim:

1. The new and distinct variety of spray carnation and parts thereof, substantially as herein shown and described, characterized by the orange coloration of its relatively small blooms produced profusely with an intermittent flowering habit, and by the vigorous and upright growth habit of the plant, reaching an average height of about 106 cm. at eight months.

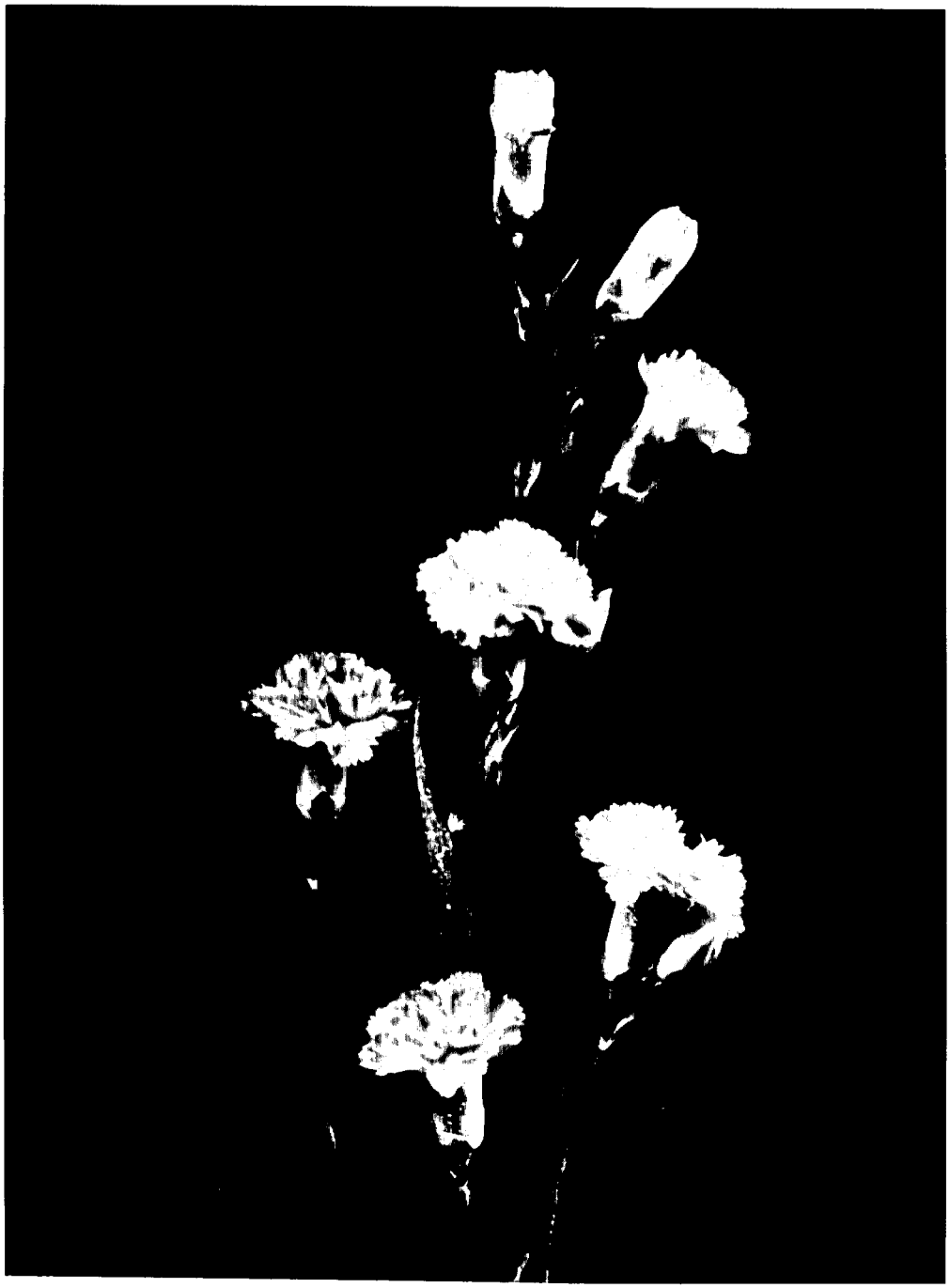

* * * * *